United States Patent [19]

Wallace

[11] Patent Number: 5,004,472
[45] Date of Patent: Apr. 2, 1991

[54] MEDICAL PRESSURE SENSING AND DISPLAY SYSTEM

[76] Inventor: William D. Wallace, 5038 Memory La., Salt Lake City, Utah 84117

[21] Appl. No.: 566,046

[22] Filed: Aug. 13, 1990

Related U.S. Application Data

[63] Continuation of Ser. No. 230,783, Aug. 10, 1988.

[51] Int. Cl.⁵ .............................................. A61M 29/02
[52] U.S. Cl. .................................... 606/194; 604/100; 600/18
[58] Field of Search ..................................... 600/16-18; 604/96-103; 606/7, 192-196

[56] References Cited

U.S. PATENT DOCUMENTS

| | | | |
|---|---|---|---|
| 4,016,871 | 4/1977 | Schiff | 600/18 X |
| 4,332,254 | 6/1982 | Lundquist | 604/99 X |
| 4,522,194 | 6/1985 | Normann | 600/18 |
| 4,651,738 | 3/1987 | Demer et al. | 606/194 |
| 4,781,192 | 11/1988 | Demer | 606/195 |
| 4,796,606 | 1/1989 | Mushika | 600/18 |
| 4,872,483 | 10/1989 | Shah | 137/557 |

Primary Examiner—John D. Yasko
Assistant Examiner—Adam J. Cermak
Attorney, Agent, or Firm—Polster, Polster and Lucchesi

[57] ABSTRACT

A fluid pressure monitoring system for a balloon catheter includes a pressure transducer in fluid communication with the interior of the balloon. The pressure transducer includes elements for providing an electrical signal which is a function of the pressure in the interior of the balloon. An electronic digital display is responsive to the electrical signal from the pressure transducer to display the balloon pressure measured by the pressure transducer. The system is especially suited for coronary angioplasty in which a catheter is inserted through blood vessels in the human body to the vicinity of a stenosis. The catheter carries an inflatable balloon to the vicinity of the stenoisis, where it is inflated, and the fluid pressure monitoring system of the present invention detects and digitally displays to the cardiologist the pressure inside the inflated balloon.

8 Claims, 3 Drawing Sheets

MEDICAL PRESSURE SENSING AND DISPLAY SYSTEM

This is a continuation of copending application Ser. No. 07/230,783, filed on Aug. 10, 1988, pending.

BACKGROUND OF THE INVENTION

This invention relates to measurement of pressures in catheter balloons and is particularly suited for measurement of such pressures in connection with coronary angioplasty catheters.

Coronary angioplasty is a rapidly growing medical procedure. In angioplasty a coronary artery which has become partially blocked by a stenosis (an abnormal narrowing of the artery due to injury or disease) is opened by inflating a balloon carried by a dilatation catheter to the site of the stenosis.

For placement purposes the dilatation catheter carries a movable guidewire which is advanced from the mouth of the respective coronary artery to the area of stenosis in the coronary artery or in one of the branches off the coronary artery. The dilatation catheter is then pushed over the guidewire to the stenosis and is placed so that the balloon carried by the dilatation catheter is disposed in the stenotic area.

The balloon at this time is collapsed so that it fits through the passage through the stenosis. The dilatation or balloon catheter typically has a pair of lumens: one through which contrast media or other suitable inflating fluid flows under pressure to inflate or deflate the balloon, and one through which the guidewire moves. When properly positioned in the stenosis, the cardiologist manually inflates the balloon by forcing contrast media through the inflation lumen into the interior of the balloon. This expansion of the balloon, assuming the size of the balloon has been chosen properly, expands the passage through the blood vessel to something approaching its normal dimensions.

It is often necessary to pressurize the balloon to a pressure in the range of from seven to ten atmospheres and to sustain this pressure for up to thirty seconds or so. During this pressurization, it is desirable to know the pressure to which the balloon is being inflated to ensure that the proper force has been applied to open the passageway. At present this pressure is displayed by an analog pressure gauge disposed in the vicinity of the syringe which is used to inflate the balloon.

Although analog pressure gauges are fairly accurate, they are not particularly easy to read, and are fairly easy to misread. These gauges are also not extremely well suited for integration into a system which can display to the cardiologist other information which would be of interest, such as elapsed time of inflation of the balloon, total desired inflation time, number of times that particular balloon has been inflated, and so on.

During coronary angioplasty the walls of the vessel are stretched and it sometimes occurs that the walls of the vessel fail under the force exerted by the expanded balloon. This incipient failure is reflected in the pressure in the balloon, but analog gauges are not especially well suited to detect this rapid change or to provide some alarm or other indication thereof to the cardiologist so that pressure could be immediately relieved before further damage to the vessel could occur.

In order to determine the actual force exerted by the balloon on the walls of the passageway, prior to the procedure cardiologists sometimes test inflate the balloon in a fixture which measures the applied force. The analog pressure gauge can be observed during this test to correlate the applied force with the pressure reading shown by the analog gauge. Analog gauges, however, are not particularly well suited to automating this test procedure.

Even if the force exerted by the balloon is not tested, the balloon is typically inflated before the procedure to ensure the patency of the balloon and to check whether the balloon can withstand the desired pressure. An analog gauge is typically used during this test to ensure that the desired pressure is applied. Such a gauge, however, is not particularly well suited to automation of this test either.

Although the problems described above arise in the connection with the coronary angioplasty procedure, it should be realized that other medical procedures involving balloon catheters have similar problems. Peripheral angioplasty, for example, is a very similar procedure with similar concerns. Other procedures in which the present invention can be used will no doubt come to mind to those of ordinary skill in the art.

SUMMARY OF THE INVENTION

Among the various objects and features of the present invention may be noted the provision of a pressure monitoring system for medical procedures which facilitates the display of balloon pressure to the user.

Another object is the provision of such a system which easily accommodates the display of additional information concerning balloon inflation to the user.

A further object is the provision of such a system which detects and warns of incipient failure of the vessel wall.

A fourth object is the provision of such a system which is especially suited for automation of various test procedures on the balloon.

Other objects and features will be in part apparent and in part pointed out hereinafter.

A system of the present invention for measuring fluid pressure in a balloon of a catheter includes a pressure transducer in fluid communication with the interior of the balloon. The pressure transducer includes an element for providing an electrical signal which is a function of the pressure in the interior of the balloon. An electronic digital display is responsive to the electrical signal from the pressure transducer to display the balloon pressure measured by the pressure transducer.

A coronary angioplasty system of the present invention includes a catheter adapted for insertion through blood vessels in the human body to the vicinity of a stenosis. The catheter carries an inflatable balloon to the vicinity of the stenosis and has an inflation lumen providing a fluid path between the interior of the balloon and an external port adapted to receive fluid for inflating the balloon. A pressure transducer is in fluid communication with the interior of the balloon, which pressure transducer includes an element for providing an electrical signal which is a function of the pressure in the interior of the balloon. An electronic digital display is responsive to the electrical signal from the pressure transducer to display the balloon pressure measured by the pressure transducer.

BRIEF DESCRIPTION OF THE DRAWINGS

Similar reference characters indicate similar parts throughout the several views of the drawings.

DESCRIPTION OF THE PREFERRED EMBODIMENTS

Figure 1:
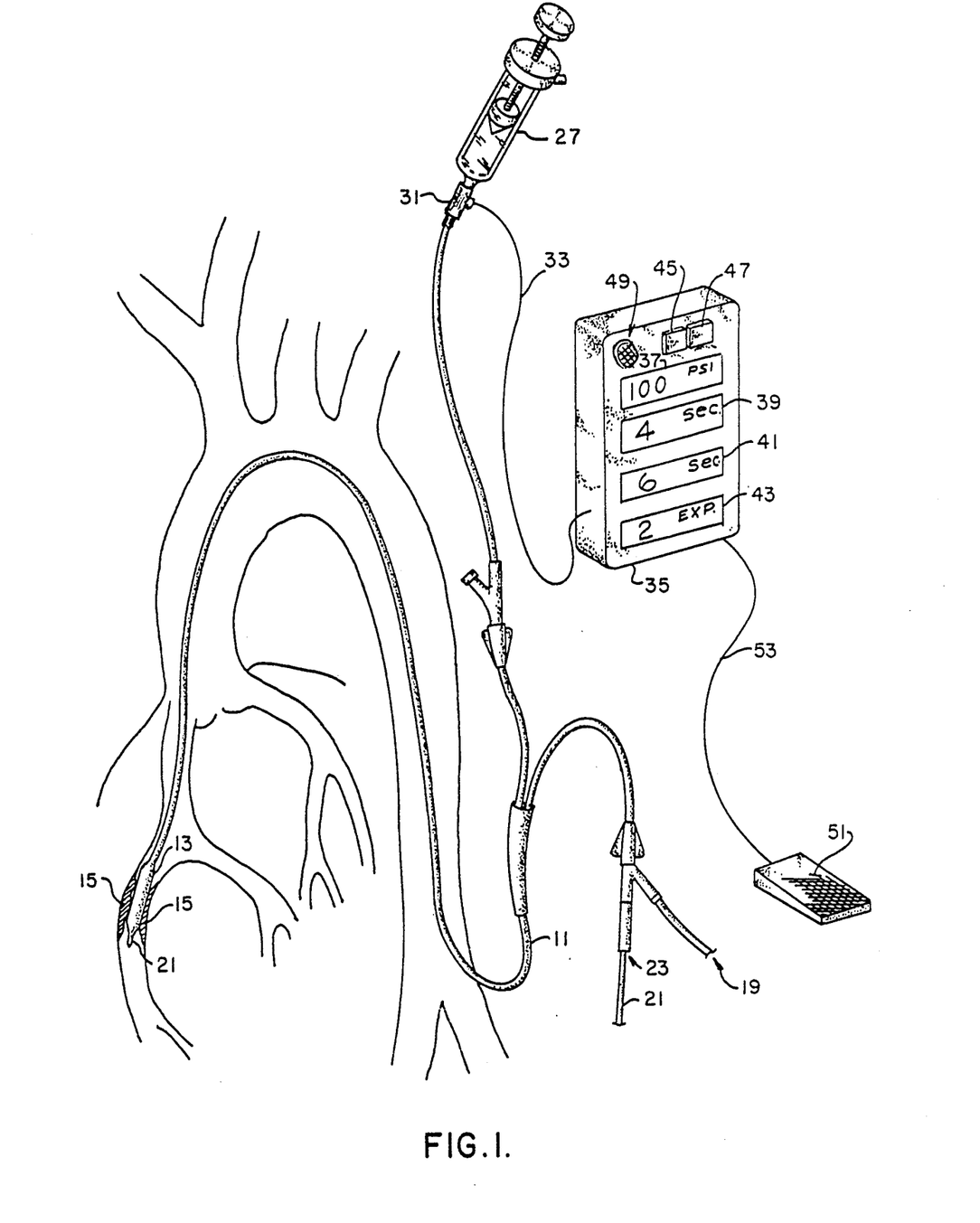
FIG. 1 is a schematical representation of the system of the present invention in use during a coronary angioplasty procedure.
Figures 2, 3:
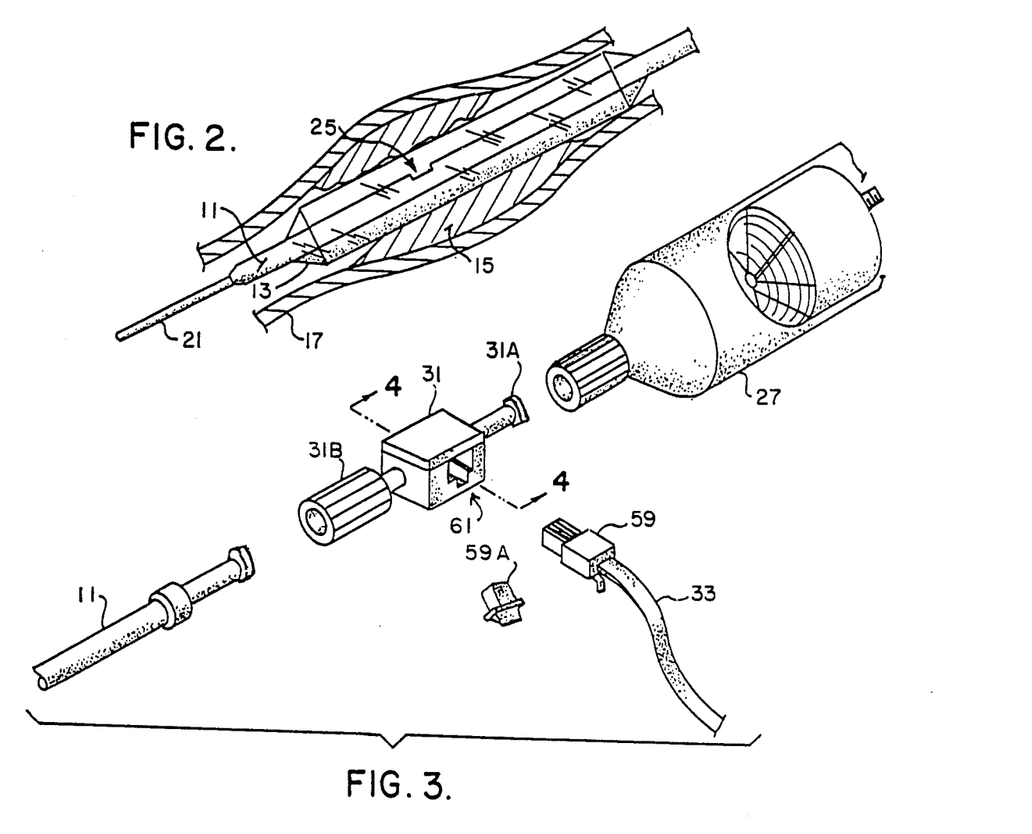
FIG. 2 is a sectional view on an enlarged scale, with parts broken away for clarity, of the opening of a stenosis by the expansion of a balloon carried by a dilatation catheter.
FIG. 3 is a perspective view illustrating the position of the pressure transducer used in the present invention in the fluid path between the source of inflating fluid and the balloon of FIG. 2.

A coronary angioplasty procedure involves a dilatation catheter 11 (FIG. 1) carrying a balloon 13 which is moved through the vascular system to the site of a stenosis 15. In FIG. 1, catheter 11 is shown passing through the aortic arch into a branch of the right coronary artery. Stenosis 15 is typically composed of atherosclerotic plaque which has partially occluded the blood vessel as shown. In FIG. 2, the balloon is shown inflated, which pushes the plaque to the sides of the passageway and, to some extent, distends the wall 17 of the vessel itself.

Catheter 11 has a pair of lumens. The first is connected to a port 19 for injection of contrast media through the catheter for purposes of positioning the catheter. That same lumen has a guidewire 21 disposed therein, guidewire 21 being inserted through a port 23 into the catheter.

The second lumen is connected by an opening 25 (FIG. 2) to the interior of balloon 13 and provides a fluid path between the interior of the balloon and an external source of balloon inflating fluid, such as the inflation/deflation syringe 27 shown in FIG. 1. Typically, such syringes have a threaded plunger which cooperates with a disengageable nut on the barrel of the syringe to permit accurate displacement of fluid (such as contrast media or any other suitable fluid) from the barrel of the syringe through the second lumen to inflate balloon 13. When the nut is disengaged, the cardiologist can quickly withdraw the piston to rapidly deflate the balloon.

Heretofore, an analog pressure gauge has been disposed in the fluid path immediately adjacent the outlet of the syringe. This gauge has provided a visual indication to the cardiologist of the actual pressure being applied to the interior of the balloon. As mentioned above, however, such analog pressure gauges have certain drawbacks associated therewith.

In the present system, a pressure transducer 29 (FIG. 4) disposed in a housing 31 (FIGS. 1, 3 and 4) is used instead of the prior art analog pressure gauges to monitor balloon pressure. Housing 31 is disposed in the inflation fluid path, specifically adjacent the outlet of the syringe. The exact placement of the transducer is not critical, so long as it is exposed to the pressure of the inflation fluid.

Pressure transducer 29 is connected by a suitable cable 33 to a housing 35 which is suitably mounted (such as on a pole, not shown) so as to be readily visible to the cardiologist. The housing carries a plurality of displays 37, 39, 41, and 43, a set of manually operable switches (two of which, labelled 45 and 47 are shown), and an alarm 49. A foot pedal 51 is electrically connected to housing 35 by a cable 53 so that the cardiologist can supply signals to the housing by that means as well.

Housing 35 contains much of the electronics of the present system. Specifically it holds a microcomputer 55 (FIG. 5) along with any necessary interface circuitry for supplying input signals to the microcomputer and control signals from the microcomputer. Although a microcomputer is shown in FIG. 5, it should be realized that discrete components could be used to control the functioning of the system of the present invention instead.

Displays 37, 39, 41, and 43 are electronic digital displays of conventional construction. Display 37 displays the balloon pressure in large, easily read characters. Although the pressure shown in FIG. 1 is in pounds per square inch, the units could as easily be atmospheres or any other suitable unit of pressure.

Display 39 displays to the cardiologist the elapsed time or duration (in seconds) for this particular expansion of the balloon. To initiate the measurement of this time by microcomputer 55, the cardiologist need only press the proper one of the manually operable switches shown, in this instance start switch 45. The timing can be stopped by pressing another switch such as switch 47 or foot pedal 51.

Figure 5:
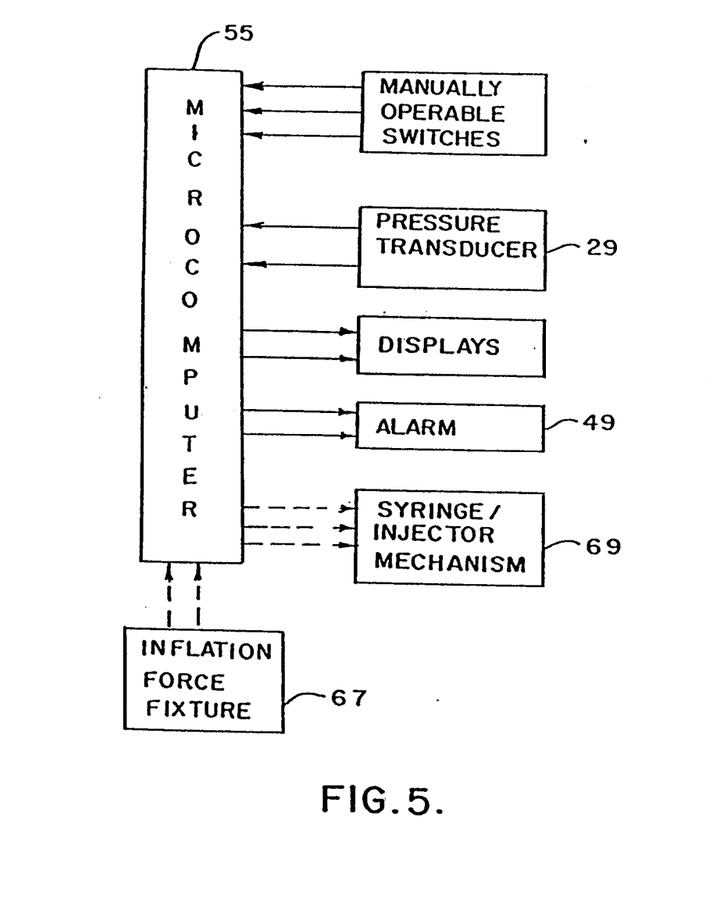
FIG. 5 is a block diagram illustrating the electrical interconnections of the system of the present invention.

Display 41 displays to the cardiologist a time (previously set by means of other manually operable switches, see FIG. 5) which represents the desired duration of this particular expansion of the balloon. For a procedure in which the balloon is expanded a number of times, it should be realized that the preset desired duration could differ for different inflations.

By comparing the output of display 39 (the actual expansion time) with the output of display 41 (the desired expansion time), the cardiologist can easily determine when to deflate the balloon.

Display 43 displays to the cardiologist the number of expansions of this particular balloon. This information is available from microcomputer 55 because the microcomputer keeps track of the interior pressure of the balloon. A measured pressure below a predetermined threshold which follows a measured pressure above that threshold signifies to the microcomputer that the balloon has been inflated and deflated. It is necessary, of course, for the user to indicate to the microcomputer by means of a manually operable switch when a catheter is replaced so that the output of display 43 may be reset.

With regard to FIG. 2, it should be noted that inflation of the balloon results in some distension of the wall 17 of the blood vessel. Should this wall start to rupture, the pressure measured by transducer 29 would rapidly change. Microcomputer 55 is fast enough to detect such a change and signal that fact to the cardiologist over alarm 49. The cardiologist upon hearing alarm 49 can then release the pressure on the balloon to prevent further rupture of the vessel wall.

Other failures such as loss of balloon patency and the like are also reflected in the pressure measured by transducer 29. Microcomputer 55 signals the occurrence of these failures over alarm 49 as well.

Figures 4, 7:
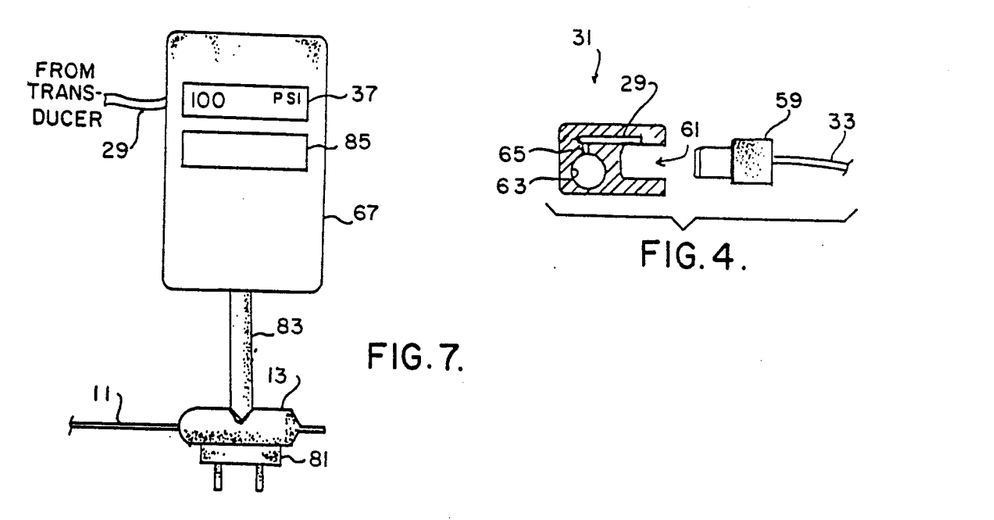
FIG. 4 is a sectional view taken along line 4—4 of FIG. 3.
FIG. 7 is a front elevational view of a dilatation catheter being tested in a force measuring fixture.

Turning to FIGS. 3 and 4, housing 31 is removably connected between syringe 27 and catheter 11 by standard leur lock fittings 31A and 31B. Electrical connection is made between transducer 29 and electronics housing 35 by means of a removable plug 59, such as a standard four-pin telephone plug, which is accepted in a corresponding socket 61 formed in housing 31. A cover 59A is provided for closing socket 61 during those times when the plug 59 is not inserted therein.

Housing 31 has a passageway 63 extending therethrough for passage of the inflating fluid from syringe 27 to catheter 11 and balloon 13. A port 65 in housing 31 extends from passageway 63 to pressure transducer 29 so that the pressure of the inflating fluid flowing through the passageway is transmitted to the pressure transducer.

Pressure transducer 29 itself is constructed in accordance with the teachings in co-assigned U.S. Pat. No. 4,610,256. The present transducer differs from the one taught in that patent only in being engineered to measure somewhat higher pressures (several atmospheres as opposed to approximately one-half atmosphere).

Port 65, as taught in U.S. Pat. No. 4,610,256 is filled with a silicone gel or oil which transmits the pressure in passageway 63 to pressure transducer 29. The transducer itself is a piezoresistive diaphragm which includes four resistive elements ion-implanted thereon in a Wheatstone bridge configuration. As is explained in U.S. Pat. No. 4,610,256, as the piezoresistive diaphragm is deflected, the resistive elements that form the Wheatstone bridge become unbalanced, thus causing electrical signals. These signals, representative of the pressure of the fluid in passageway 63, are sent to microcomputer 55 via plug 59.

This connection of the pressure transducer with microcomputer 55 is illustrated in FIG. 5. Of course, the signal received from the pressure transducer may be filtered, temperature compensated, etc. as is well known in the art. For the purposes of this invention, however, the important fact is that the microcomputer acquires inflating fluid pressure information from pressure transducer 29.

Also shown in FIG. 5 are the other significant inputs to and outputs from microcomputer. The inputs include the manually operable switches such as switches 45, 47 and foot pedal 51, the pressure transducer (discussed above), and an input from an inflation force fixture 67 (described below in connection with FIG. 7). The outputs include control signals for the displays (which includes displays 37, 39, 41, and 43), for the alarm 49, and for a syringe/injector mechanism 69 described below in connection with FIG. 6.

Microcomputer 55 is under programmed logic control to govern the system to operate as described above. In response to actuation of the proper manually operable switches, it begins timing and displaying (on display 39) the duration of a balloon inflation. It also, at short intervals, reads the signal from pressure transducer 29 and displays the sensed pressure on display 37. If a desired inflation duration has been set, it also displays this time on display 41, and increments the balloon inflation count on display 43.

If a pressure change is detected during the procedure which would indicate some failure (either of the vessel wall or of the catheter itself), microcomputer 55 sounds alarm 49.

Figure 6:
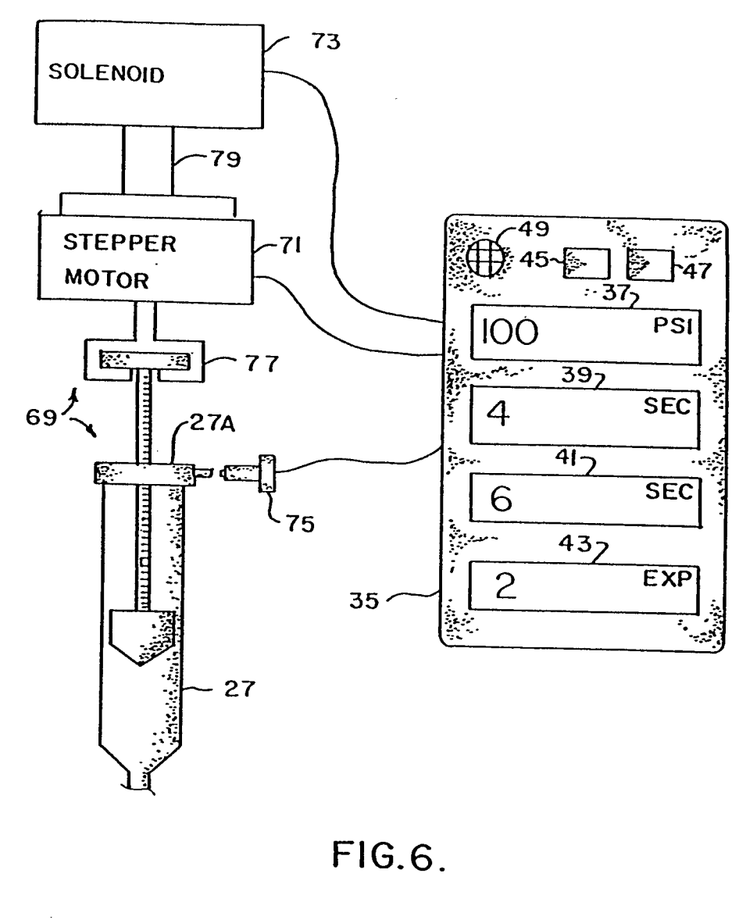
FIG. 6 is a perspective view of an alternative embodiment of the system of the present invention.

If desired, the process of injecting the inflating fluid into the balloon and of deflating the balloon can also be controlled by the microcomputer. Such a system is shown in FIG. 6. In addition to having the inputs and outputs of the system of FIG. 1 (omitted in this FIG. for clarity), the system of FIG. 6 also includes outputs for controlling a stepper motor 71, a solenoid 73 and a syringe release arm 75.

The microcomputer provides control signals to stepper motor 71 to cause the motor to operate. Motor 71 is connected by a fitting 77 to the plunger of syringe 27, so that operation of motor 71 causes the plunger to force inflating fluid out of the syringe and (via the inflation lumen of catheter 11) into balloon 13. The microcomputer monitors the pressure during this operation, so that once the desired pressure is reached operation of the stepper motor is stopped.

The microcomputer maintains the balloon pressure at this preset amount until the preset duration for that balloon expansion expires. Upon the expiration of that time, microcomputer 55 operates stepper motor 71 in the reverse direction to deflate the balloon. In the event that more rapid deflation of the balloon is need, the microcomputer activates arm 75 to move from its position shown in FIG. 6 to an operating position (not shown) in which is releases the threaded nut or cap 27A of the syringe so that the plunger may be rapidly withdrawn with respect to the barrel of the syringe.

Actual rapid withdrawal of the plunger is accomplished by solenoid 73. The solenoid is secured to motor 71 by a shaft 79. Operation of the solenoid draws the shaft, along with the stepper motor and the plunger of syringe 27 upwardly to rapidly withdraw the inflating fluid from balloon 13.

One condition in which the microcomputer rapidly withdraws the plunger, for example, is when the microcomputer detects a pressure change indicative of some failure condition during the inflation phase of the procedure. It should be realized that the microcomputer is capable of responding to such a failure situation much more rapidly and reliably that could a human operator of the syringe.

Although the invention has been described heretofore with reference to the actual coronary angioplasty procedure, it has equal applicability to the preliminary testing of the balloon before actual insertion into the patient. It can readily be seen how the apparatus of FIG. 1 or the apparatus of FIG. 6 is usable to preliminarily inflate the balloon before insertion into the patient to test the patency of the balloon. That apparatus, or more specialized apparatus shown in FIG. 7, may also be used to correlate the balloon pressure with the force applied by the balloon.

Such a force/pressure correlating apparatus includes a backing plate 81 upon which the balloon of the catheter under test is disposed. A force sensing arm 83 is lifted by the pressure in the balloon, and the corresponding force exerted by the balloon is measured by a transducer (not shown). Microcomputer 55 then displays on display 37 and on an additional display 85 the pressure in the balloon (obtained from pressure transducer 29) and the resulting force on force sensing arm 83. With this apparatus the pressure and force are easily correlated, and the force information may be recorded by microcomputer 55 for future reference, if desired.

In view of the above it will be seen that the various objects and features of the present invention are achieved and other advantageous results attained. The described embodiments are illustrative only and the present invention is defined instead by the claims which are appended hereto.

Having thus described the invention, what is claimed and desired to be secured by Letters Patent is:

1. A system for measuring fluid pressure in a balloon of a catheter, said balloon being adapted for inflation inside a vessel in a human body, said catheter having an inflation lumen providing a fluid path between the interior of the balloon and an external source of fluid for inflating the balloon, said system comprising:

a pressure transducer in fluid communication with the interior of the balloon, said pressure transducer including means for providing an electrical signal which is a function of the pressure in the interior of the balloon;

electronic digital display means operatively connected to said transducer and responsive to the electrical signal from the pressure transducer for digitally displaying the balloon pressure measured by the pressure transducer; and means for timing the actual duration of the application of pressure to the interior of the balloon for each inflation of the balloon, said timing means being responsive to a predetermined initiation signal to initiate timing, said electronic digital display means including means operatively connected to and responsive to the timing means for digitally displaying the actual duration of the application of pressure to the interior of the balloon for each inflation of the balloon.

2. A system for measuring fluid pressure in a balloon of a catheter, said balloon being adapted for inflation inside a vessel in a human body, said catheter having an inflation lumen providing a fluid path between the interior of the balloon and an external source of fluid for inflating the balloon, said system comprising:

a pressure transducer in fluid communication with the interior of the balloon, said pressure transducer including means for providing an electrical signal which is a function of the pressure in the interior of the balloon;

electronic digital display means operatively connected to said transducer and responsive to the electrical signal from the pressure transducer for digitally displaying the balloon pressure measured by the pressure transducer;

means for timing the actual duration of the application of pressure to the interior of the balloon for each inflation of the balloon, said timing means being responsive to a predetermined initiation signal to initiate timing, said electronic digital display means including means operatively connected to and responsive to the timing means for digitally displaying the actual duration of the application of pressure to the interior of the balloon for each inflation of the balloon; and manually operable means operatively connected to said electrical digital displaying means for presetting a desired duration of the application of pressure to the interior of the balloon, said electronic digital display means including means responsive to the manually operable means for digitally displaying the desired duration.

3. The system as set forth in claim 2 wherein the digital display means includes means for displaying (a) the balloon pressure, (b) the actual duration of the application of pressure, and (c) the desired duration on separate digital displays simultaneously.

4. The system as set forth in claim 3 wherein the balloon pressure display, the actual duration display, and the desired duration display are generally adjacent each other.

5. A system for measuring fluid pressure in a balloon of a catheter, said balloon being adapted for inflation inside a human body, said catheter having an inflation lumen providing a fluid path between the interior of the balloon and an external source of fluid for inflating the balloon, said system comprising:

a pressure transducer in fluid communication with the interior of the balloon, said pressure transducer including means for providing an electrical signal which is a function of the pressure in the interior of the balloon;

electronic digital display means operatively connected to said transducer and responsive to the electrical signal from the pressure transducer for digitally displaying the balloon pressure measured by the pressure transducer; and means operatively connected to said pressure transducer for recording the number of inflations of the balloon, said electronic digital display means including means operatively connected to the recording means for digitally displaying the recorded number of inflations of the balloon.

6. The system as set forth in claim 5 wherein the digital display means includes means for displaying the balloon pressure and the number of balloon inflations on separate digital displays simultaneously.

7. The system as set forth in claim 6 wherein the balloon pressure display and the number of balloon inflations display are generally adjacent each other.

8. A system for measuring fluid pressure in a balloon of a catheter, said balloon being adapted for inflation inside a vessel in a human body, said catheter having an inflation lumen providing a fluid path between the interior of the balloon and an external source of fluid for inflating the balloon, said system comprising:

a pressure transducer in fluid communication with the interior of the balloon, said pressure transducer including means for providing an electrical signal which is a function of the pressure in the interior of the balloon;

electronic digital display means operatively connected to said transducer and responsive to the electrical signal from the pressure transducer for digitally displaying the balloon pressure measured by the pressure transducer;

means operatively connected to said transducer and responsive to the electrical signal from the pressure transducer for recording the pressure represented by the signal; and means operatively connected to said transducer for digitally timing the actual duration of the application of pressure to the interior of the balloon for each inflation of the balloon, said recording means including means operatively connected to said timing means and responsive to the timing means for recording said duration.

* * * * *

REEXAMINATION CERTIFICATE (2494th)
United States Patent [19]
Wallace

[11] B1 5,004,472
[45] Certificate Issued  Feb. 28, 1995

[54] MEDICAL PRESSURE SENSING AND DISPLAY SYSTEM

[75] Inventor: William D. Wallace, Salt Lake City, Utah

[73] Assignee: Utah Medical Products, Inc., Midvale, Utah

Reexamination Request:
No. 90/003,246, Nov. 5, 1993

Reexamination Certificate for:
Patent No.: 5,004,472
Issued: Apr. 2, 1991
Appl. No.: 566,046
Filed: Aug. 13, 1990

Related U.S. Application Data

[63] Continuation of Ser. No. 230,783, Aug. 10, 1988, Pat. No. 5,021,046.

[51] Int. Cl.$^6$ .............................................. A61M 29/02
[52] U.S. Cl. .................................... 606/194; 604/100; 600/18
[58] Field of Search ...................................... 600/16–18, 600/7, 192–196; 604/96–103, 118–121

[56] References Cited
U.S. PATENT DOCUMENTS

| | | |
|---|---|---|
| D. 266,695 | 10/1982 | Trammll et al. . |
| 383,940 | 6/1888 | Brinkerhoff . |
| 404,105 | 5/1889 | Overlach . |
| 446,125 | 2/1891 | Schirmer . |
| 577,682 | 2/1897 | Eissner . |
| 730,054 | 6/1903 | Sheets . |
| 1,661,818 | 3/1928 | Cook . |
| 1,707,880 | 4/1929 | Sheets . |
| 2,656,836 | 10/1953 | Hickey . |
| 2,672,866 | 2/1954 | Kater . |
| 2,699,168 | 1/1955 | Lewis . |
| 2,736,315 | 2/1956 | Feeney . |
| 3,080,866 | 3/1963 | Friedman . |
| 3,388,941 | 6/1968 | Marcus . |
| 3,478,937 | 11/1969 | Solowey . |
| 3,491,757 | 1/1970 | Arce . |
| 3,720,199 | 3/1973 | Rishton et al. . |
| 3,834,394 | 9/1974 | Hunter et al. . |
| 3,985,123 | 10/1976 | Herzlinger et al. . |
| 4,019,523 | 4/1977 | Clark et al. . |
| 4,057,050 | 11/1977 | Sarstedt . |
| 4,062,373 | 12/1977 | Clark et al. . |
| 4,063,662 | 12/1977 | Drummond et al. . |
| 4,254,773 | 3/1981 | Waldbillig . |
| 4,256,461 | 3/1981 | Wallace et al. . |
| 4,261,360 | 4/1981 | Perez . |
| 4,267,846 | 5/1981 | Kontos . |
| 4,285,340 | 8/1981 | Gezari et al. . |
| 4,331,156 | 5/1982 | Apple et al. . |
| 4,370,982 | 2/1983 | Reilly . |
| 4,402,307 | 9/1983 | Hanson et al. . |
| 4,409,986 | 10/1983 | Apple et al. . |
| 4,439,185 | 3/1984 | Lundquist . |
| 4,439,186 | 3/1984 | Kuhl . |
| 4,444,335 | 4/1984 | Wood et al. . |
| 4,446,867 | 5/1984 | Leveen et al. . |
| 4,460,355 | 7/1984 | Layman . |
| 4,466,426 | 8/1984 | Blackman . |
| 4,568,335 | 2/1986 | Updike et al. . |
| 4,572,208 | 2/1986 | Cutler et al. . |
| 4,576,181 | 3/1986 | Wallace et al. . |
| 4,583,974 | 4/1986 | Kokernak . |
| 4,592,364 | 6/1986 | Pinto . |
| 4,601,037 | 7/1986 | McDonald . |
| 4,619,269 | 10/1986 | Cutler et al. . |
| 4,655,749 | 4/1987 | Fischione . |
| 4,658,829 | 4/1987 | Wallace . |
| 4,662,355 | 5/1987 | Pieronne et al. . |
| 4,664,125 | 5/1987 | Pinto . |
| 4,697,574 | 10/1987 | Karcher et al. . |
| 4,706,670 | 11/1987 | Andersen et al. . |
| 4,710,179 | 12/1987 | Haber et al. . |
| 4,715,854 | 12/1987 | Vaillancourt . |
| 4,723,556 | 2/1988 | Sussman . |
| 4,723,938 | 2/1988 | Goodin et al. . |
| 4,756,706 | 7/1988 | Kerns et al. . |
| 4,758,223 | 7/1988 | Rydell . |
| 4,777,951 | 10/1988 | Cribier et al. . |
| 4,781,192 | 11/1988 | Demer . |
| 4,785,822 | 11/1988 | Wallace . |
| 4,787,368 | 11/1988 | Kageyama . |
| 4,794,910 | 1/1989 | Mushika . |
| 4,796,606 | 1/1989 | Mushika . |
| 4,815,472 | 3/1989 | Wise et al. . |
| 4,820,271 | 4/1989 | Deutsch . |

| | | |
|---|---|---|
| 4,825,876 | 5/1989 | Beard . |
| 4,832,692 | 5/1989 | Box et al. . |
| 4,865,581 | 9/1989 | Lundquist et al. . |
| 4,872,483 | 10/1989 | Shah . |
| 4,873,986 | 10/1989 | Wallace . |
| 4,877,035 | 10/1989 | Bogen et al. . |
| 4,887,608 | 12/1989 | Mohl et al. . |
| 4,899,741 | 2/1990 | Bentley et al. . |
| 4,899,761 | 2/1990 | Brown et al. . |
| 4,909,069 | 3/1990 | Albin et al. . |
| 4,934,996 | 6/1990 | Mohl et al. . |
| 4,949,723 | 8/1990 | Wallace et al. . |
| 4,966,161 | 10/1990 | Wallace et al. . |
| 4,969,470 | 11/1990 | Mohl et al. . |
| 5,011,468 | 4/1991 | Lundquist et al. . |
| 5,019,041 | 5/1991 | Robinson et al. ............ 604/97 |
| 5,021,046 | 6/1991 | Wallace . |
| 5,024,668 | 6/1991 | Peters et al. . |
| 5,046,965 | 9/1991 | Neese et al. . |
| 5,059,167 | 10/1991 | Lundquist et al. . |
| 5,084,060 | 1/1992 | Freund et al. . |
| 5,135,488 | 8/1992 | Foote et al. . |
| 5,147,300 | 9/1992 | Robinson et al. ............ 604/97 |

FOREIGN PATENT DOCUMENTS

| | | |
|---|---|---|
| 545415 | of 0000 | Canada . |
| 0149866A2 | of 0000 | European Pat. Off. . |
| 0446932A2 | of 0000 | European Pat. Off. . |
| WO90/11040 | of 1990 | WIPO . |
| WO92/15361 | of 1992 | WIPO . |

OTHER PUBLICATIONS

Reference Catalog—Schneider—Shiley, Nov. 1987.
Pheripheral, Product Catalog—Schneider, Nov. 1990.
Peripheral Division—Schneider.
Cardiology Product Catalog—Schneider, May 1991.
Guideline From The Leader—Schneider.
The Next Generation PTCA Catheter Series For Overachievers Everywhere—Schneider.
When Complex Anatomy Demands A Simplified Approach—Advanced Cardiovascular Systems, Inc.
Catalog—Mansfield.
New Softip 5 & 6 French High Flow Braided Polyrethane Catheters . . . "Angiomedics Inc. Max Trak D. P." Mansfield.
Hydracross TLC PTCA Catheter Specifications—Baxter, Edwards LIS Division.
Catheters From Clinical Instruments—Clinical Instruments Corp.
Multilumen Central Venous Catheters.
Balloon Occlusion Catheters—Clinical Instruments Corp.
Isoflo Precision Flow Control Disposable Manifolds—Healthdyne Cardiovascular Inc.
Max Trak D.P.—Mansfield.
The Cordis Hand Injector—Cordis Corporation.
New Product Bulletin, Leveen Inflator With Pressure Guage—Medi—Tech, Boston Scientific Corporation.
Simply Compare—Scimed, Life Systems, Inc.
New Indeflator Plus 20—Advanced Cardiovascular Systems, Inc.
Veri—Cal (Cazia) and Time Ramp Generator-Apr. 20, 1989.
Morse Manifold for Angiography—Manic, Angiographic Systems Division.
The Perceptor Morse Manifold—Namic, Angiographic Systems Division.
The Perceptor DT—Namic, Angiographic Systems Division.
Reusable Morse Manifolds—Namic, Angiographic Systems Division.
Sosa Pressurized Delivery System—Namic, Angiographic Systems Division.
Namic Flexcil Flexible High Pressure Contrast Injection Lines—Namic, Angiographic Systems Division.
Namic 10CC Angiographic Syringe Family—Namic, Angiographic Systems Division.
The Namic 10CC Angiographic Syringe Palm Pad Family—Namic, Angiographic Systems Division.
Morse High Pressure Stopcocks 1050 PSI Rated—Namic, Angiographic Systems Division.
Namic Custom Angiographic Kits—Namic, Angiographic Systems Division.
Namic PTCA Kit—Namic, Angiographic Systems Division.
The Namic Protection Station—Namic, Angiographic Systems Division.
Namic Angio—Sac—Namic, Angiographic Systems Division.
Homer Mammalok Plus—Namic, Angiographic Systems Division.
Hawkins Universal Drainage Set—Namic, Angiographic Systems Division.

Welcome to the Merit Monarch Coronation.
Intellsystem Software Changes.
Certified Supplier Program—Advanced Cardiovascular Systems, Inc.
Looking for People with Vision—Advanced Cardiovascular Systems, Inc.
Medflator—Medex Inc.
The New 7F Triguide Guiding Catheter—Scimed.
ACS Assessories Offer Optimum Efficiency in Your Angioplasty Procedures—Advanced Cardiovascular Systems, Inc.
Angioplasty—Tristate Magazine, David Beasley.
Coronary Angioplasty—Krames Communications.
Good News for People with Only Two Hands—Scimed, Life Systems Inc.
New Caution on the Heart Balloon—U.S. News & World Report, Jul. 25, 1988.
PTCA Safe and Efficacious Performed Together with Diagnostic Angiography in Selected Cases—Cardiovascular News, May 1988.
Inflation Pro—Baxter Healthcare Corporation.
USCI Wizard Disposable Inflation Device—Bard, USCI Division.
Medflator—Medex Inc.
Digiflator—Vastek.
Digiflator—Mansfield, Boston Scientific Corporation.
Intelliflator—Merit Medical.
Condor Transflator Infrared System—Condor Medical.
In Vivo Assessment of Vascular Dilation During Percutaneous Transluminal Coronary Angioplasty—The American Journal of Cardiology, Jain et al.
Clinical Trial of the Disposable Transducer Catheter—Catherization and Cardiovascular Diagnosis 14:63-68 (1988), Se Do Cha et al.
Ballooning Out Gets Mostly Good Marks—May 16, 1987, D. D. Edwards.
Total Control—Vastek.
The Accuracy of Today's MSOT Sophisticated Microprocessors has been Merged with the Sensitity of the Clinician's Hand to Bring a New Level of Control to Angioplasty Procedures—Vastek.
System Specifications—Vastek.
Model 4×4 Replacement Head—Peerless.
Serumax Medical Robotics—Serumax.
Clamp Ease for Initial Hemostasis Post-Arteriotomy—Pressure Productgs Inc.
The Use of Pressure—Volume Curves to Assess the Mechanism and Adequacy of Stenosis Dilation by Balloon Angioplasty—Demer et al., Kardiologie (1987).
Total Control Intercom System—Vastek.
Reach Out and "Touch" The Future—Vastek.
Now, Fetal Monitoring is a Snap—Utah Medical Products Inc.
Medical Firm Offers New Product ... —Deseret News, Nov. 1991.
Sherlock—Merit Medical Systems.
NKK Series JB Keypad Switches—NKK Switches.
PD75328/75P328 4-Bit Microcomputers with LCD Controller/Driver and A/D Converter—NEC Electronics Inc.
MPX2700 Series—Motorola Inc.
Finesse Electro Surgery and Smoke Evacuation System—Utah Medical Products Inc.
The Only Complete Line of IUP Catheters—Utah Medical Products Inc.
Disposa-Hood Infant Oxygen Hood—Utah Medical Products Inc.
Pressure Monitoring Kits—Utah Medical Products Inc.
Deltran II & Delta-Cal—Utah Medical Products Inc.
ACS Product Catalog—Advanced Cardiovascular Systems Inc.
Built for Speed—Bard, USCI Division.
The Dilating Guidewire (DGW)—Scimed, Life Systems Inc.
Laser Technology and Balloon Angioplasty: Research and Development—James Grabek.
Laser Angioplasty: A European View—Docteur E. Zeitler.
Intellisystem—Merit Medical Systems Inc.
Sensym Pressure Sensors—Sensym.
Pressure Sensors—Micro Switch, a Honeywell Division.

*Primary Examiner*—C. Fred Rosenbaum

[57] ABSTRACT

A fluid pressure monitoring system for a balloon catheter includes a pressure transducer in fluid communication with the interior of the balloon. The pressure transducer includes elements for providing an electrical signal which is a function of the pressure in the interior of the balloon. An electronic digital display is responsive to the electrical signal from the pressure transducer to display the balloon pressure measured by the pressure transducer. The system is especially suited for coronary angioplasty in which a catheter is inserted through blood vessels in the human body to the vicinity of a stenosis. The catheter carries an inflatable balloon to the vicinity of the stenoisis, where it is inflated, and the fluid pressure monitoring system of the present invention detects and digitally displays to the cardiologist the pressure inside the inflated balloon.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2-7 is confirmed.

Claims 1 and 8 are determined to be patentable as amended.

New claims 9-18 are added and determined to be patentable.

1. A system for measuring fluid pressure in a balloon of a catheter, said balloon being adapted for inflation inside a vessel in a human body, said catheter having an inflation lumen providing a fluid path between the interior of the balloon and an external source of fluid for inflating the balloon, said system comprising:
   a pressure transducer in fluid communication with the interior of the balloon, said pressure transducer including means for providing an electrical signal which is a function of the pressure in the interior of the balloon;
   electronic digital display means operatively connected to said transducer and responsive to the electrical signal from the pressure transducer for digitally displaying the balloon pressure measured by the pressure transducer; and
   means for timing the actual duration of the application of pressure to the interior of the balloon for being responsive to a predetermined initiation signal to initiate timing, *and a predetermined stop signal to stop timing, such that the display means displays said actual duration for a substantial period of time,* said electronic digital display means including means operatively connected to and responsive to the timing means for digitally displaying the actual duration of the application of pressure to the interior of the balloon for each inflation of the balloon.

8. A system for measuring fluid pressure in a balloon of a catheter, said balloon being adapted for inflation inside a vessel in a human body, said catheter having an inflation lumen providing a fluid path between the interior of the balloon and an external source of fluid for inflating the balloon, said system comprising:
   a pressure transducer in fluid communication with the interior of the balloon, said pressure transducer including means for providing an electrical signal which is a function of the pressure in the interior of the balloon;
   electronic digital display means operatively connected to said transducer and responsive to the electrical signal from the pressure transducer for digitally displaying the balloon pressure measured by the pressure transducer;
   means operatively connected to said transducer and reponsive to the electrical signal from the pressure transducer for recording, *for future reference,* the pressure represented by the signal; and
   means operatively connected to said transducer for digitally timing the actual duration of the application of pressure to the interior of the balloon for each inflation of the balloon, said recording means including means operatively connected to said timing means and responsive to the timing means for recording said duration.

*9. A system as set forth in claim 1 wherein said electronic digital display means includes means for digitally displaying the number of inflations of the balloon.*

*10. The system as set forth in claim 9 wherein the digital display means includes means for displaying the balloon pressure and the number of balloon inflations on separate digital displays simultaneously.*

*11. The system as set forth in claim 10 wherein the balloon pressure display and the number of balloon inflations display are generally adjacent each other.*

*12. A system as set forth in claim 8 further comprising means operatively connected to said pressure transducer for recording the number of inflations of the balloon, said electronic digital display means including means operatively connected to the recording means for digitally displaying the recorded number of inflations of the balloon.*

*13. The system as set forth in claim 12 wherein the digital display means includes means for displaying the balloon pressure and the number of balloon inflations on separate digital displays simultaneously.*

*14. The system as set forth in claim 13 wherein the balloon pressure display and the number of balloon inflations display are generally adjacent each other.*

*15. A system for measuring fluid pressure in a balloon of a catheter, said balloon being adapted for inflation inside a vessel in a human body, said catheter having an inflation lumen providing a fluid path between the interior of the balloon and an external source of fluid for inflating the balloon, said system comprising:*
   *a pressure transducer in fluid communication with the interior of the balloon, said pressure transducer including means for providing an electrical signal which is a function of the pressure in the interior of the balloon;*
   *electronic digital display means operatively connected to said transducer and responsive to the electrical signal from the pressure transducer for digitally displaying the balloon pressure measured by the pressure transducer; and*
   *means for timing the actual duration of the application of pressure to the interior of the balloon for each inflation of the balloon, said timing means being responsive to a predetermined initiation signal to initiate timing and being responsive to a predetermined ending signal to stop timing, said electronic digital display means including means operatively connected to and responsive to the timing means for digitally displaying a value corresponding to the time at which the predetermined ending signal occurs such that the actual duration of the application of pressure to the interior of the balloon for the current inflation of the balloon is displayed.*

*16. A system as set forth in claim 15 wherein said electronic digital display means includes means for digitally displaying the number of inflations of the balloon.*

*17. A system for measuring fluid pressure in a balloon of a catheter, said balloon being adapted for inflation inside a vessel in a human body, said catheter having an inflation* lumen providing a fluid path between the interior of the balloon and an external source of fluid for inflating the balloon, said system comprising:

a pressure transducer in fluid communication with the interior of the balloon, said pressure transducer including means for providing an electrical signal which is a function of the pressure in the interior of the balloon;

electronic digital display means operatively connected to said transducer and responsive to the electrical signal from the pressure transducer for digitally displaying the balloon pressure measured by the pressure transducer;

means operatively connected to said transducer and responsive to the electrical signal from the pressure transducer for recording for later the pressure represented by the signal; and means operatively connected to said transduer for digitally timing the actual duration of the application of pressure to the interior of the balloon for each inflation of the balloon, said recording means including means operatively connected to said timing means and responsive to the timing means for recording said duration and storing said duration for future reference.

18. A system as set forth in claim 17 further comprising means operatively connected to said pressure transducer for recording the number of inflations of the balloon, said electronic digital display means including means operatively connected to the recording means for digitally displaying the recorded number of inflations of the balloon.

* * * * *